Figure 1:
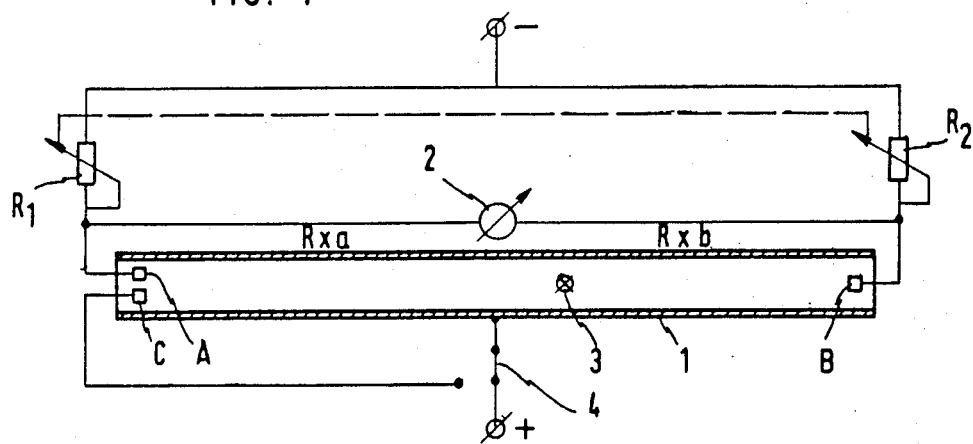

United States Patent [19]

Trampert

[11] Patent Number: 4,912,418

[45] Date of Patent: Mar. 27, 1990

[54] METHOD AND DEVICE FOR DETECTING THE LOCATION OF A FAULT WITHIN A DIELECTRIC LAYER OF AN ELECTRICALLY CONDUCTING PIPE

[75] Inventor: Rainer Trampert, Oftersheim, Fed. Rep. of Germany

[73] Assignee: Pfaudler-Werke AG, Schwetzingen, Fed. Rep. of Germany

[21] Appl. No.: 206,271

[22] Filed: Jun. 13, 1988

[30] Foreign Application Priority Data

Jun. 26, 1987 [DE] Fed. Rep. of Germany ....... 3721205

[51] Int. Cl.$^4$ .................. G01M 3/16; G01R 31/12
[52] U.S. Cl. ........................ 324/557; 324/559; 324/514
[58] Field of Search ............ 174/11 R; 324/557, 558, 324/559, 514, 522, 526, 512

[56] References Cited

U.S. PATENT DOCUMENTS 3,365,661 1/1968 Zimmerman ............ 324/526
3,555,414 1/1971 Deichelmann .
3,800,217 3/1974 Lowrance ............... 324/557
4,161,688 7/1979 Nakayama .............. 324/526

FOREIGN PATENT DOCUMENTS 3201643 7/1983 Fed. Rep. of Germany ...... 324/526
0163446 12/1981 Japan ................... 324/557
0044864 3/1982 Japan ................... 324/526

Primary Examiner—Reinhard J. Eisenzopf
Assistant Examiner—Jose M. Solis
Attorney, Agent, or Firm—Robert P. Simpson; Michael L. Dunn

[57] ABSTRACT

A method and a measuring device for localizing a damage in a dielectric corrosion resistant layer of a pipe line are described, especially for an enameled pipe line, through which an electrolytically conducting fluid is passed. Localization is achieved by performing a potential difference measurement between two electrodes arranged at the begining and at the end of a supervised region along the length of the pipe line, to which preferably a constant current source is connected, the positive terminal of which is connected with the carrier material of the pipe line and the negative terminal of which is connected with the two electrodes. Preverably a calibration is performed by means of an additional electrode, which can be connected to the measurement region.

26 Claims, 1 Drawing Sheet

METHOD AND DEVICE FOR DETECTING THE LOCATION OF A FAULT WITHIN A DIELECTRIC LAYER OF AN ELECTRICALLY CONDUCTING PIPE

The invention is related to a method for detecting a damage of a corrosion-resistant dielectric protective layer of a pipe line having an electrically conducting wall, especially for an enameled pipe line through which an electrolytically conducting medium is conveyed, as well as a measuring device for performing the method.

A method of this type is already known, in which for detecting a damage in the enamel layer of an enameled apparatus a continuous supervision is performed, in order to detect a damage of the layer immediately upon its occurrence by means of current changes (DE-PS No. 1 293 478). In this method a direct current source is connected with its positive terminal to the electrically conducting carrier material and with its other terminal to an enameled measuring electrode, in order to measure a damage-current, so that a damage occurring during operation can be detected immediately. If such a damage is not recognized soon, a corrosion of the carrier material can be caused in the region of the damage, so that not only a contamination of the product with iron can be caused, which cannot be allowed in certain cases, but also a penetration of the wall of the apparatus can be caused after a rather short time, with the consequence that a leakage of the product occurs, which can be quite dangerous or the reason for pollution. Such a supervision for an early detection of damages can also be performed in such a manner, that a chemical analysis is performed for determining the iron contents of the final product. As soon as iron is found in the product, the production is stopped.

In the case of both mentioned method the difficulty exists, that it is often not possible, to determine the location, at which the damage occurred in the corrosion resistant layer. This difficulty is practically quite significant if such methods are used for supervising rather long pipe lines, which may have a length of some hundred meters and may comprise a large number of tubes connected with each other to form the pipe line. In order to determine the location of the damage it is necessary in such cases, to separate the tubes of the pipe line and to test each single tube, in order to find the actually damaged tube. A damage at the respective tube may be detected by means of a high voltage test device. However, since such a testing method needs much time and causes remarkable work, it would be desirable to reduce as far as possible stoppage time and necessary work for localizing a damage. If a certain contamination of the product is acceptable, actually the possibility exists, to wait until a leakage of the fluid product can be recognized, so that only the respective tube has to be replaced. However, this would necessitate great efforts, in order to limit dangers of the above mentioned kind to a remaining risk considered as tolerable.

Therefore, a problem to be solved by the invention is to be seen in the fact, that a method and a measuring device for detecting of a damage in a dielectric corrosion resistant layer of a pipe line shall be improved in such a manner, that only rather simple means and provisions are necessary for localizing a detected damage immediately upon its recognition, in order to avoid disadvantages and difficulties of the mentioned type.

This problem is solved in the case of a method of the above mentioned type, in which either an electric or analytical supervision can be performed for recognizing a damage. A measuring device for performing such a method is also provided by the present invention. Advantageous embodiments of the invention and further developments of the invention are subject of the subclaims.

Specific advantages of the invention are therefore to be seen in the fact, that immediately upon recognition of a damage, the damage can be localized by measuring a potential difference occurring between the two measuring electrodes, which define the range of measurement. Thereby it is even possible in the case of a pipe line having a length of e.g. 200 meters, to find the specific tube of the numerous tubes, in which tube the damage occurred. It is then only necessary to replace the respective tube, so that only rather little work and a rather short stoppage of production is caused, whilst on the other hand a pollution-danger can be avoided.

Figure 2:
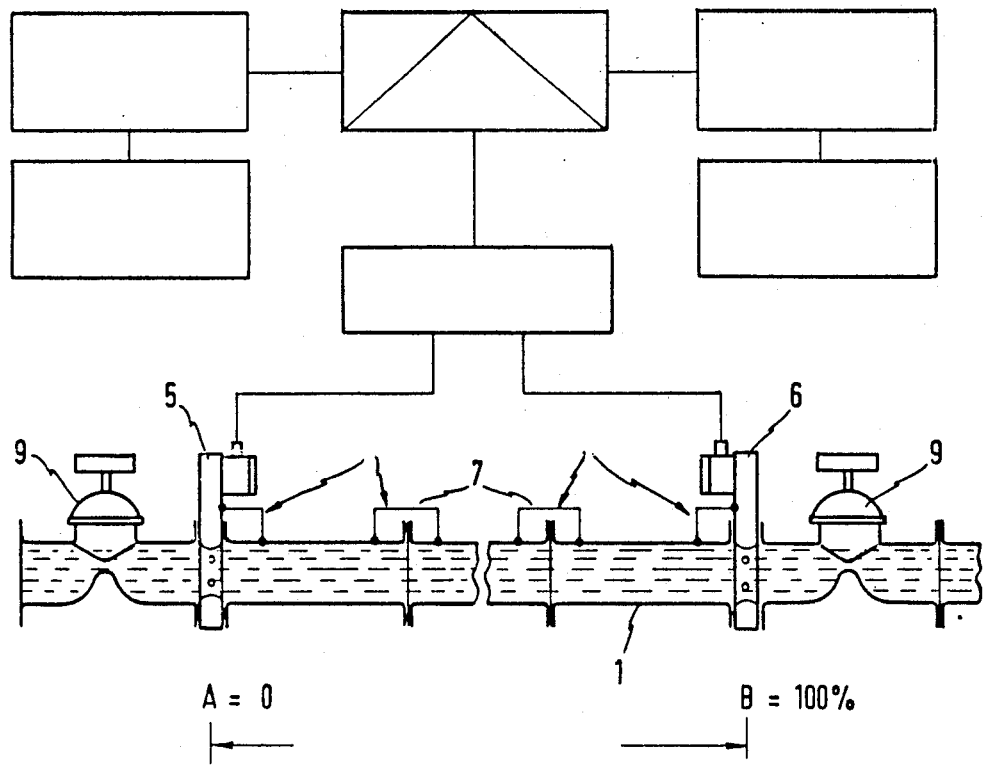

On the basis of the drawings a specific embodiment of the invention shall be described. In the drawings:

FIG. 1 shows a diagramatic representation for explaining the method in accordance with the invention, and FIG. 2 shows a diagramatic representation for explaining the measuring device in accordance with the invention.

In the schematic embodiment as shown in FIG. 1 a pipe line 1 is provided, which is coated by an enamel layer on its inner surface. The pipe line may have a length of some hundred meters. The pipe line 1 therefore comprises a corresponding number of tube-units, which are fixed with each other by flange connections. The carrier material of the tubes is e.g. mild steel. The single tube-units are connected with each other in an electrically conducting manner. The length of the pipe line to which a method and a measuring device in accordance with the invention are applied, may be up to about 500 meters. The maximum length of the region to be supervised along the length of the tube line depends on the electrical conductivity of the fluid conducted through the pipe line.

At the begin of the supervised region along the length of the pipe line an electrode A is embedded, and on the end of the supervised region an electrode B is embedded into the enamel layer. The two measuring electrodes A and B consist out of a metal like rhodium, platinum or gold, or of another material which is corrosion resistant for the respective purpose of use.

Besides one of the two measuring electrodes A, B preferably a third electrode C is provided, which serves as a calibrating electrode. The three electrodes are shaped similar in the shown embodiment, so that the electrodes substantially have identical contact surfaces with the electrolytrically conducting fluid which is passed through the pipe line.

Connected with the electrically conducting carrier material of the pipe line 1 is the positive terminal of a constant current source, the negative terminal of which is connecte with the two measuring electrodes A and B through resistors R1 and R2. The two resistors R1 and R2 are part of a tandem-potentiometer and have the same value of resistance. Across the measurement region defined by the two measuring electrodes A and B a voltmeter 2 is connected.

The occurrence of a damage 3 in the enamel layer which results in a contact between the fluid and the carrier material of the enameled tube line 1, is detected by a continuous supervision in known manner.

In the following the method according to the invention shall be explained. Upon detection of a damage on the basis of a continuous supervision, to the two measuring electrodes A und B a constant current of about 0.5 to 10 mA direct current is applied. The amperage of the constant current depends on the length of the measuring distance and on the conductivity of the fluid. For performing the measuring method conductivities of the fluid of more than about 500 μS are generally necessary. Because of the damage 3 an electrically conducting connection results through the fluid between the measuring electrodes A and B through the respective location of the damage 3 to the electrically conducting carrier material of the pipe line 1. In the bridge circuit as used in this embodiments therefore partial resistance Rxa and Rxb exist between the measuring electrode A and the location of the damage, and the measuring electrode B and the location of the damage 3, resp. A potential difference measurement between the two measuring electrodes A and B therefore allows to determine the position of the damage 3 along the region of measurement between the two measuring electrodes.

For calibration the measuring device the calibration electrode C is connected with the positive terminal of the constant current source by a calibration switch 4. With the tandem potentiometer with the two equal resistors R1 and R2 the potential difference between the connected electrodes is calibrated to 100% (full deflection at voltmeter 2). In this manner it can be achieved, that during measuring of the potential difference between the two measuring electrodes a reduction of the deflection of the pointer of the voltmeter takes place, which is direct proportional to the distance of the position of the damage from the respective measuring electrode to the centerpoint of the pipe line. Though it is not absolutely necessary to provide an additional calibration electrode C for calibrating, the use of such an electrode is advantageous, since otherwise an erroneous indication of about 10% could arise because of the direct contact. The schematic representation of the calibration switch 4 in FIG. 1 is furthermore to be understood in such a manner, that during calibrating the positive terminal of the constant current source is not connected with the carrier material of the pipe line 1.

As may be seen from the embodiment in FIG. 2 a pipe line 1 of the kind of interest normally consist out of a larger number of tube units, which are connected with each other by flange connections, so that mass connections 7 are provided for electrically connecting the tube units. The electrodes may be provided directed at the respective tube units, or may be provided in intermediate rings 5, 6 enameled on their inner surfaces and inserted between respective tube units, in order to define the region of the measurement. In order to provide pipe line with a measuring device in accordance with the invention, which pipe lines have already been used in production, respective tube units can be replaced by tube units serving as electrode carrier. Alternatively, intermediate pieces serving as electrode carriers can be inserted. Such measuring regions may be provided in such sections, in which an increased danger for the occurrence of damages exists, e.g. behind an outlet valve or before another valve.

Upon recognition of a damage and before its localization it is furthermore advantageous and in certain cases even necessary, to separate the measuring region before performing the measuring of the potential difference, by closing two valves, which are provided directly before and behind the measuring region. In this manner it can be avoided that shunting occurs, which can be caused e.g. by not isolated metallic built-in elements like tantalum plugs in a connected reactor.

The term pipe line is to be understood in such manner, that also cascades of heat exchanger tubes or columns or the like elements having the same diameter are included.

The embodiment as shown in FIG. 2 related to the measuring device contains a measuring electronic, to which a control is associated, so that with the same measuring device a recognition of the damage is possible as well as a localization of the position of the damage upon recognition of a damage. As an example, during localizing such an evaluation can be performed, that it can be indicated by means of a display device, which tube unit is having a damage and therefore has to be replaced. Furthermore, an adjustment of the measuring region can be performed before or after the occurrence of a damage. The connection of the positive terminal of the constant current source with the carrier material in FIG. 1 is generally necessary, if depositions by electrolysis shall be or have to be avoided.

In certain cases, however, also a reverse polarity is possible, and in contrast to the preferred embodiment with a constant current source a constant voltage source can be provided with both possible polarities. It is also possible to use alternate voltage or alternate current.

I claim:

1. A device for detecting the location of a fault within a dielectric layer comprising the inner surface of an electrically conducting pipe, through which a conducting fluid is passed, comprising:
   (a) a first variable upper impedance connected between a first node and a third node where said third node is defined as comprising fluid within the pipe at a first position in said pipe;
   (b) a second variable upper impedance adjusted to have an impedance value equal to said first upper impedance and connected between said first node and a fourth node where said fourth node is defined as comprising fluid within the pipe at a second position in said pipe;
   (c) a first lower impedance comprised of conducting fluid within said pipe between said third node in said pipe and a fault within said dielectric, wherein said fault comprises a point of continuity between the conducting fluid and the conducting pipe and also comprises a second node;
   (d) a second layer impedance comprised of conducting fluid within said pipe between the fourth node in said pipe and said fault of said dielectric layer;
   (e) means for applying a constant current between said first and second nodes when said fault occurs; and,
   (f) means for measuring a potential difference between said third and fourth nodes.

2. The device of claim 1 wherein said means for measuring a potential difference is a voltmeter.

3. The device of claim 1 wherein said first and second upper impedances are variable resistors.

4. A method for detecting the location of a fault within a dielectric layer comprising the inner surface of an electrically conducting pipe, through which an electrically conducting fluid is passed, using a bridge circuit having four nodes, comprising:

(a) applying a constant current between a first node and a second node when a fault occurs within said dielectric layer, wherein said second node is located at a position on said conducting pipe where said fault occurs;

(b) measuring a potential difference between a third node and a fourth node of said circuit, wherein said first and third nodes are connected by a first variable upper impedance and said first and fourth nodes are connected by a second variable upper impedance adjusted to have an impedance value equal to said first upper impedance, wherein said third node is defined as comprising fluid within the pipe at a first position in said pipe and said fourth node is defined as comprising fluid within the pipe at a second position in said pipe; and (c) determining the location of said fault from said measured potential difference.

5. The method of claim 4 wherein said third and fourth nodes define a measuring region.

6. The method of claim 5 further comprising the step of closing a region of the pipe containing the measuring region before performing the measurement of the potential difference.

7. The method of claim 4 including the step of calibrating a measuring device for measuring the potential difference between said third and fourth nodes.

8. The method of claim 7 wherein the calibration is such that a reduction of the measured potential difference is proportional to a distance from the center of said pipe to the point of damage.

9. The method of claim 4 wherein said third and fourth nodes are located at opposite ends of said pipe.

10. The method of claim 4 wherein said measured potential difference is related to a distance from the center of a length of said pipe to said location of said fault.

11. The method of claim 4 wherein said measured potential difference is proportional to a distance from the center of a length of said pipe to said location of said fault.

12. The method of claim 4 wherein the magnitude of said constant current is adjusted dependent upon the length of the pipe and the conductivity of the conducting fluid.

13. The method of claim 12 wherein said constant current is adjusted to provide current of approximately 0.5 milliamperes to about 10 milliamperes when said dielectric layer is damaged.

14. A bridge circuit having four nodes for detecting the location of a fault within a dielectric layer comprising the inner surface of an electrically conducting pipe, through which a conducting fluid is passed, comprising:

(a) means for applying a constant current between a first node and a second node when a fault occurs within said dielectric layer, wherein said second node is located at a position on said conducting pipe where said fault occurs;

(b) means for measuring a potential difference between a third node and a fourth node of said circuit, wherein said first and third nodes are connected by a first variable upper impedance and said first and fourth nodes are connected by a second variable upper impedance adjusted to have an impedance value equal to said first upper impedance, wherein said third node is defined as comprising fluid within the pipe at a first position in said pipe and said fourth node is defined as comprising fluid within the pipe at a second position in said pipe; and (c) means for determining the location of said fault from said measured potential difference.

15. The device of claim 14 wherein said measured potential difference is related to a distance from the center of a length of said pipe to the location of said fault.

16. The device of claim 14 wherein said measured potential difference is proportional to a distance from the center of a length of said pipe to the location of said fault.

17. The device of claim 14 wherein the magnitude of said constant current is adjusted dependent upon the length of the pipe and the conductivity of the conducting fluid.

18. The device of claim 17 wherein said constant current is adjusted to provide current of approximately 0.5 milliamperes to about 10 milliamperes when said dielectric layer is damaged.

19. The device of claim 14 wherein said third and fourth nodes define a measuring region.

20. The device of claim 19 further comprising means for closing a region of the pipe line containing the measuring region before performing the measurement of the potential difference.

21. The device of claim 14 including means for calibrating a measuring device for measuring the potential difference between said third and fourth nodes.

22. The device of claim 21 wherein the calibration is such that a reduction of the measured potential difference is proportional to a distance from the center of a length of said pipe to the location of said fault.

23. The device of claim 14 wherein said third and fourth nodes are located at opposite ends of said pipe.

24. The device of claim 21 wherein the means for calibrating a measuring device comprises a calibrating electrode, said calibrating electrode being in contact with said fluid and being connected by a switch with a measuring region.

25. The device of claim 24 wherein the third and fourth nodes and the calibrating electrode are embedded into a dielectric layer of intermediate rings being fixed at a beginning and at an end of a supervised region.

26. The device of claim 24 wherein areas of contact surfaces of the embedded third and fourth nodes and the calibrating electrode with the conducting fluid are predetermined and substantially similar.

* * * * *